United States Patent [19]

Sisson

[11] 4,020,117
[45] Apr. 26, 1977

[54] ADSORPTIVE RECOVERY SYSTEM FOR METHYL CHLORIDE AND METHYLENE CHLORIDE

[75] Inventor: Richard M. Sisson, Washougal, Wash.

[73] Assignee: Stauffer Chemical Company, Westport, Conn.

[22] Filed: Aug. 14, 1975

[21] Appl. No.: 603,842

Related U.S. Application Data

[63] Continuation of Ser. No. 517,694, Oct. 24, 1974, abandoned, which is a continuation of Ser. No. 317,891, Dec. 26, 1972, abandoned, which is a continuation-in-part of Ser. No. 68,266, Aug. 21, 1970, abandoned.

[52] U.S. Cl. .................. 260/652 P; 260/659 A; 260/662 A; 55/59; 55/74
[51] Int. Cl.² ........................................ C07C 17/38
[58] Field of Search ....... 260/652 P, 659 A, 662 A, 260/654 S; 55/59, 74

[56] References Cited

UNITED STATES PATENTS

| | | | |
|---|---|---|---|
| 2,957,924 | 10/1960 | Heiskell | 260/662 |
| 3,148,041 | 9/1964 | Dehn et al. | 260/652 P |
| 3,426,086 | 2/1969 | Gray et al. | 260/652 P |

FOREIGN PATENTS OR APPLICATIONS

| | | | |
|---|---|---|---|
| 1,075,823 | 7/1967 | United Kingdom | 260/652 P |

Primary Examiner—D. Horwitz
Attorney, Agent, or Firm—Michael J. Bradley

[57] ABSTRACT

Recovery of methyl chloride and methylene chloride from a chlorination reactor effluent by use of a novel adsorption sysem is disclosed. The incorporation of this novel system into an oxychlorination process is also covered.

12 Claims, 3 Drawing Figures

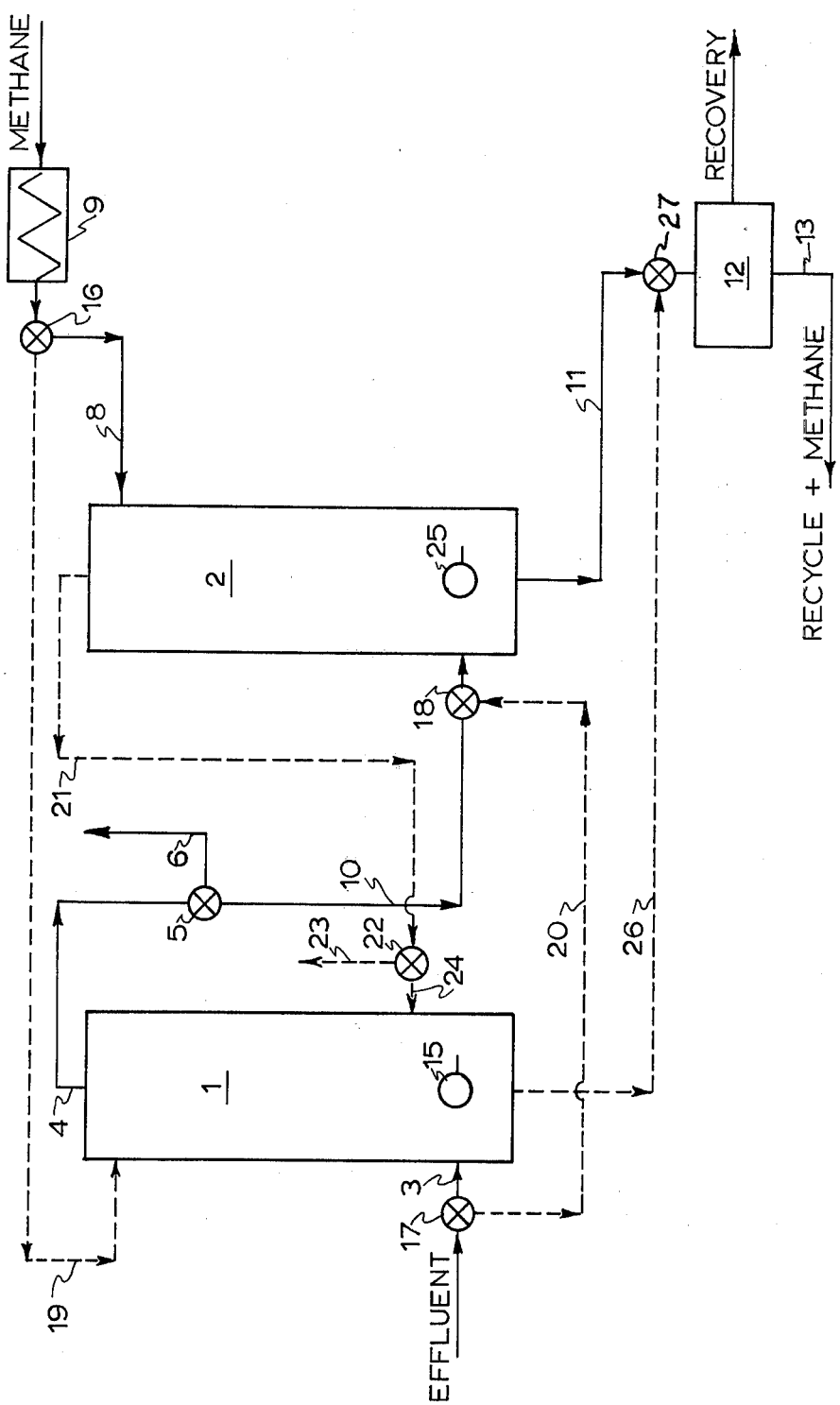
FIGURE #1

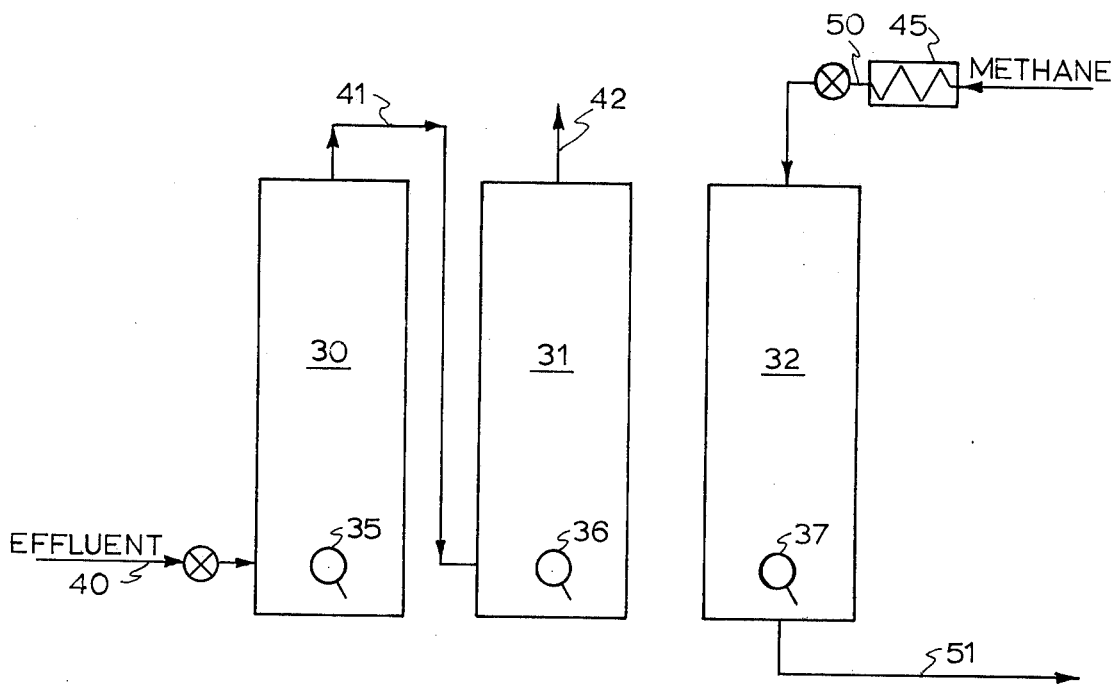
FIGURE #2
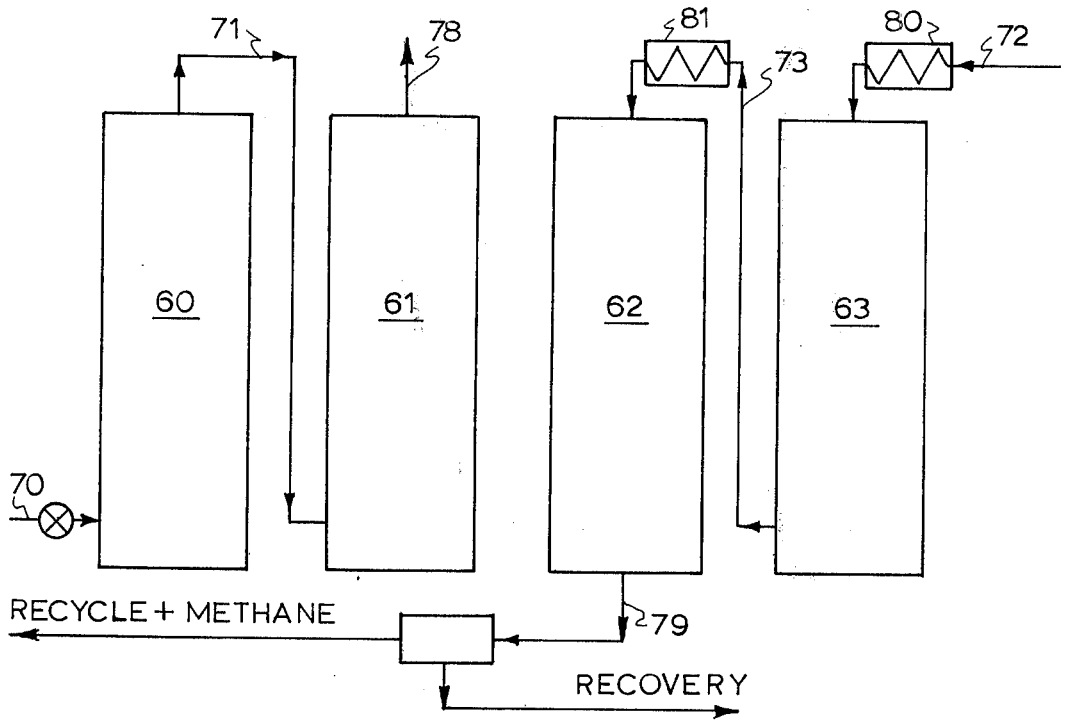
FIGURE #3
INVENTOR.
RICHARD M. SISSON
BY Albert J. Adamcik
ATTORNEY

ADSORPTIVE RECOVERY SYSTEM FOR METHYL CHLORIDE AND METHYLENE CHLORIDE

This is a continuation of application Ser. No. 517,694, filed Oct. 24, 1974, now abandoned, which is a continuation of application Ser. No. 317,891, filed Dec. 26, 1972, now abandoned, which is a continuation of application Ser. No. 68,266, filed Aug. 31, 1970, now abandoned.

BACKGROUND OF THE INVENTION

The present invention relates to a method of recovering methyl chloride and methylene chloride. More particularly, the invention relates to the recovery of methyl chloride and methylene chloride from gaseous mixtures containing significant amounts of relatively noncondensable gases produced in the chlorination of methane. In its preferred form, the invention relates to the recovery of methyl chloride and methylene chloride from cooled reactor effluents extant in that type of methane chlorination process described as "oxychlorination". The invention also comprises a novel process for the oxychlorination of methane which features improved and economical recovery of methyl chloride and methylene chloride.

Although the chlorination of methane with $Cl_2$ or HCl is known in the art, frequently there are serious operational problems generally associated with this type of reaction. For example, considerable difficulty may be experienced in oxychlorination processes in the recovery of the chlorinated methanes issuing from the reaction. One reason for this problem is the fact that the chlorinated methane products are likely to be diluted in great or significant quantities of inert or relatively noncondensable gases such as nitrogen, carbon monoxide, HCl, carbon dioxide, and other similar gases. In order to recover the products satisfactorily from such a process, it would be necessay to process great quantities of gas and efficiently recover the chlorinated methane content thereof. This may be accomplished by a "condensation" step; or series of steps, in which the gaseous chlorination or oxychlorination reactor effluent is cooled, for example, by contacting the effluent with a cooling medium, such as chilled water or other cooling liquids, followed by separation of the liquid and gaseous phases.

While condensation of large volumes of chlorinated methanes in such a fashion is technologically feasible, the procedure is complicated due to the low boiling characteristics of methyl chloride and methylene chloride. A typical oxychlorination reactor effluent, after the "condensation" or cooling step or steps, may contain roughly, by weight, based on the total weight of the effluent, from about one to about twenty percent methyl chloride, from trace amounts (0.01 per cent or less) to about 10 percent methylene chloride, and from negligible or trace amounts up to five percent of chloroform and carbon tetrachloride combined. In order to remove the methyl chloride and methylene chloride from the effluent, after the aforementioned "condensation" step or steps, expensive additional cooling would be necessary, thus rendering the complete recovery of these low-boiling materials uneconomical. In the case of oxychlorination processes, the relatively high freezing point of $CO_2$ poses additional problems.

SUMMARY OF THE INVENTION

The invention encompasses a novel and economical process for the recovery of methyl chloride and methylene chloride from a cooled methane chlorination reactor effluent containing significant amounts of relatively noncondensable gases comprising passing the cooled reactor effluent to an adsorption stage to adsorb the methyl chloride and methylene chloride, stripping the methyl chloride and methylene chloride from the adsorption stage by the use of heated methane feed, and subsequently cooling the adsorption stage, as more particularly hereinafter specified. In particular, the invention comprises a process for recovering methyl chloride and methylene chloride from a cooled methane chlorination reactor effluent, comprising (a) feeding the cooled methane chlorination reactor effluent to a first adsorption stage to adsorb methyl chloride and methylene chloride until a desired amount of the methyl chloride and methylene chloride is adsorbed and producing a lean reactor effluent; (b) stopping the flow of the cooled methane chlorination reactor effluent to the first adsorption stage and feeding the cooled reactor effluent to a second adsorption stage to adsorb methyl chloride and methylene chloride until a desired amount of the methyl chloride and methylene chloride is adsorbed and producing a lean reactor effluent, while simultaneously desorbing methyl chloride and methylene chloride adsorbed in the first adsorption stage with all or part of the methane feed to the chlorination reactor, and recovering the methyl chloride and methylene chloride and the methane feed, and then cooling the first adsorption stage with the lean reactor effluent from the second adsorption stage. The method of the invention is particularly adapted to cyclic operation wherein the lean reactor effluent from the first adsorption stage is used to cool the second adsorption stage after the second adsorption stage has been desorbed, and wherein the lean reactor effluent from the second adsorption stage, when it is in its adsorption phase, is used to cool the first adsorption stage after it has been desorbed.

In a preferred form of the invention, methyl chloride and methylene chloride are recovered from cooled methane chlorination reactor effluent by (a) feeding the cooled methane chlorination reactor effluent to a first adsorption stage to adsorb methyl chloride and methylene chloride until a desired amount of the methyl chloride and methylene chloride is adsorbed, and producing a lean reactor effluent; (b) stopping the flow of the cooled methane chlorination reactor effluent to the first adsorption stage and feeding said cooled reactor effluent to a second adsorption stage to adsorb methyl chloride and methylene chloride until a desired amount is adsorbed, producing a lean reactor effluent, while simultaneously desorbing the methyl chloride and methylene chloride adsorbed in the first adsorption stage with methane feed to the chlorination reactor, and recovering the methyl chloride and methylene chloride and methane feed; (c) stopping the flow of the cooled methane chlorination reactor effluent to the second adsorption stage and then feeding said cooled reactor effluent to a third adsorption stage to adsorb methyl chloride and methylene chloride until a desired amount is adsorbed, and producing a lean reactor effluent, while simultaneously desorbing the methyl chloride and methylene chloride adsorbed in the second adsorption stage with methane feed to the chlorination reactor, and cooling the first adsorption stage with the lean reactor effluent from the third adsorption stage, and recovering the methyl chloride and methylene chloride, and methane feed. As indicated, the method of the invention is especially suited to cyclic operation wherein the lean reactor effluent from the first adsorption stage is used to cool the second adsorption stage after the second adsorption stage has been desorbed, the lean reactor effluent from the second adsorption stage, while in its adsorption phase, is used to cool the third adsorption stage after the third adsorption stage has been desorbed, and the lean reactor effluent from the third adsorption stage, while in its adsorption phase, is used to cool the first adsorption stage after the third adsorption stage has been desorbed.

In its more preferred form, the invention relates to a process for recovering methyl chloride and methylene chloride, from a cooled methane chlorination reactor effluent comprising (a) feeding the cooled methane chlorination reactor effluent to a first adsorption stage to adsorb methyl chloride and methylene chloride until a desired amount is adsorbed, and producing a lean reactor effluent; (b) stopping the flow of the cooled methane chlorination reactor effluent to the first adsorption stage and feeding said cooled reactor effluent to a second adsorption stage to adsorb methyl chloride and methylene chloride until a desired amount is adsorbed, producing a lean reactor effluent, while simultaneously beginning desorption of the methyl chloride and methylene chloride adsorbed in the first adsorption stage with methane feed to the chlorination reactor, and recovering the methyl chloride and methylene chloride, and methane feed; (c) stopping the flow of the cooled methane chlorination reactor effluent to the second adsorption stage and feeding said cooled effluent to a third adsorption stage to adsorb methyl chloride and methylene chloride until a desired amount is adsorbed, and producing a lean reactor effluent, while simultaneously beginning desorption of the methyl chloride and methylene chloride adsorbed in the second adsorption stage with heated methane feed to the chlorination reactor, and completing the desorption of the methyl chloride and methylene chloride adsorbed in the first adsorption stage, and recovering the methyl chloride and methylene chloride and methane feed; (d) stopping the flow of the cooled methane chlorination reactor effluent to the third adsorption stage and feeding the cooled effluent to a fourth adsorption stage to adsorb methyl chloride and methylene chloride until a desired amount is adsorbed, and producing a lean reactor effluent; while simultaneously beginning desorption of the methyl chloride and methylene chloride adsorbed in the third adsorption stage with heated methane feed to the chlorination reactor, completing the desorption of the methyl chloride and methylene chloride, adsorbed in the second adsorption stage, and cooling the first adsorption stage with the lean reactor effluent from the third adsorption stage. This embodiment of the invention is similarly eminently adaptable to a cyclic operation in which the lean reactor effluent from the first adsorption stage is used to cool the second adsorption stage after the second adsorption stage has been desorbed, the lean reactor effluent from the second adsorption stage, while in its adsorption phase, is used to cool the fourth adsorption stage after the fourth adsorption stage has been desorbed, the lean reactor effluent from the third adsorption stage, while in its adsorption phase, is used to cool the first adsorption stage, and the lean reactor effluent from the fourth adsorption stage, while in its adsorption phase, is used to cool the third adsorption stage.

The process of the invention is particularly advantageous in that the use of the cooled lean reactor effluent from the adsorption phase for cooling the adsorption stage undergoing its cooling phase reduces the need for additional cooling means. Similarly, the use of the methane feed for the chlorination reactor provides improved efficiency with respect to heat considerations and total recovery or utilization of the methyl chloride and methylene chloride. As will be appreciated by those skilled in the art, trace or minor amounts, up to five percent by weight (combined) of chloroform and carbon tetrachloride may also be adsorbed and removed by the process of the invention.

DETAILED DESCRIPTION OF THE INVENTION

In to demonstrate the invention more fully, reference is made to FIG. 1 of the accompanying drawing. Cooled chlorination reactor effluent having a temperature of from about −60°C. to about 10° C. passes through valve 17 and line 3 into adsorber 1, where methyl chloride and methylene chloride, and any residual or minor amounts of chloroform or carbon tetrachloride in the effluent are adsorbed on an adsorbent such as activated carbon. Simultaneously, methane heated to a temperature of from about 100° to about 300° C. in heat exchanger 9 is passed through line 8 by operation of valve 16 and into adsorber 2 to strip methyl chloride and methylene chloride, and chloroform or carbon tetrachloride adsorbed in a previous operation. The methyl chloride, methylene chloride, and methane are passed out of adsorber 2 through line 11 and valve 27. The methane and stripped materials may then be treated optionally in two ways: through a separation stage 12, such as a condenser or an adsorber, to separate the stripped materials from the methane as liquids, to the extent desired, or the stream may pass directly through line 13 to the chlorination reactor so that the methyl chloride and methylene chloride may be further chlorinated. Under some operating conditions, it may be desirable to recirculate the gases in line 13 back through the heat exchanger 9 by means of a recirculatory blower (not illustrated).

Returning to adsorber 1, as the cooled chlorination reactor effluent passes through the adsorber and the low boiling constituents (i.e., methyl chloride and methylene chloride) and any residual chloroform and carbon tetrachloride are adsorbed on the adsorbent, the now lean effluent passes out of adsorber 1 through line 4 and through valve 5. Valve 5 is opened or closed depending on the stage of the regeneration (stripping) process in adsorber 2. While adsorber 2 is undergoing the regeneration or stripping operation, valve 5 is closed and the lean effluent from adsorber 1 in line 4 is vented through line 6, or sent to be utilized elsewhere in the operation. However, when the regeneration of adsorber 2 by the heated methane is complete, valve 16 is closed, stopping the flow of heated methane, valve 5 is opened, and the lean effluent from line 4 passes through line 10 and valve 18 and into adsorber 2 to cool adsorber 2. When the desired loading of adsorber 1 has been accomplished and adsorber 2 has been regenerated and cooled, valve 17 in line 3 is operated to divert the cooled chlorination reactor effluent stream through line 20 and through valve 18. Valve 18 is actuated to stop the flow from line 10 and to pass the reactor effluent in line 20 into the regenerated and cooled adsorber 2. All flow lines in this stage are shown in dotted lines. Simultaneously, valve 16 is actuated and methane now passes through line 19 into adsorber 1 to begin regenerating adsorber 1. From adsorber 2, the stripped reactor effluent, which is now devoid of the methyl chloride and methylene chloride, passes out line 21 and through valve 22 to vent line 23. However, as with adsorber 2 previously, when adsorber 1 becomes regenerated, valve 16 is closed, and valve 22 is opened, and the lean effluent then passes through line 24 into adsorber 1 in order to effect the cooling of adsorber 1 prior to the next adsorption stage.

During the regeneration of adsorber 1, methane and the stripped materials leave adsorber 1 through line 26 and pass through three-way valve 27. The stream is then treated as above indicated. Cooling means 15 and 25, such as cooling coils, may be employed in adsorbers 1 and 2 to provide additional cooling.

FIG. 2 represents an embodiment of the invention wherein more effective utilization of the cooling power of the lean reactor effluent is made. The 3-stage operation is more advantageous in that it allows more effective use of the lean reactor effluent gas from the adsorber as a cooling medium, and reduces the necessity of extra cooling means.

In order to avoid confusion due to illustration of an excess number of lines and valves, etc., the system of FIG. 2 is represented at only one phase of its cyclic operation. Those skilled in the art, however, can readily supply the proper mechanization, given the basic pattern and flow information disclosed herein. In this phase, adsorber 30 is in the adsorption phase; adsorber 31 is in the cooling phase; and adsorber 32 is in its regeneration or stripping phase. Cooled methane chlorination reactor effluent passes through line 40 into adsorber 30, wherein the methyl chloride, methylene chloride, and any residual chloroform and carbon tetrachloride are adsorbed. The lean reactor effluent is then passed through line 41 overhead to adsorber 31 where it serves to cool adsorber 31, which has been heated from a previous regeneration phase, and the effluent is then vented through line 42. At this point, adsorber 32 is in its regeneration phase, and fresh feed methane passes through heat exchanger 45, through line 50, and into adsorber 32 to strip the methyl chloride, etc., which have been adsorbed in a previous adsorption phase. The methane and stripped materials leave adsorber 32 through line 51 and may then be sent directly into the chlorination reactor, or may be sent to an intermediate separation stage such as a condenser or adsorber in which the stripped materials are removed to the extent desired before the stream is sent to the chlorination reactor. As with the embodiment of FIG. 1, it may be desirable under some operating conditions to recirculate the gases in line 51 back through heat exchanger 45 by means of a recirculatory blower (not shown). As will be appreciated by those skilled in the art, in the next phase of the operation, adsorber 31 receives the cooled methane chlorination reactor effluent from line 40, while adsorber 30 undergoes regeneration with methane from line 50, and adsorber 32 receives the lean reactor effluent from adsorber 31, and is thereby cooled. In the final phase of the operation, adsorber 32 receives the cooled methane chlorination reactor effluent from line 40 while adsorber 30 undergoes cooling by the lean effluent from adsorber 32, and adsorber 31 is now regenerated by the heated methane from line 50. After this stage, the cycle begins anew to assure continuous, efficient removal. Each of adsorbers 30, 31 and 32 may be provided with additional cooling means 35, 36 and 37. The use of the threestage system as proposed provides improved efficiency in the use of the lean reactor effluent from the respective adsorption phase.

In the preferred form of the invention, there is provided a bank of four adsorbers. This design utilizes effectively the lean reactor gas coming from the given adsorption phase to cool the adsorber undergoing the cooling phase, and two adsorbers are simultaneously in the stripping stage. Referring more particularly to FIG. 3 of the drawing, at a given stage of the sequence, the flow pattern is as follows: cooled methane chlorination reactor effluent passes through line 70 and into the adsorber 60. The overhead lean reactor effluent gas, now stripped of the methyl chloride and methylene chloride, and any residual chloroform or carbon tetrachloride, passes through line 71 and into adsorber 61, which it cools, and then is vented through line 78. Simultaneously, feed methane passes through line 72, is heated in heater exchanger 80, and then enters adsorber 63 which is in its final step of the stripping phase. The heated methane completes the stripping or regeneration of adsorber 63, leaves adsorber 63 through line 73, is reheated, if necessary, in optional exchanger 81, and passes through adsorber 62, to begin its regeneration. The methane and stripped materials then pass through line 79 and may be sent either to the chlorination reactor or through a separation stage, such as a condenser or adsorber, where a portion or all of the stripped materials is separated, as desired.

As will be appreciated by those skilled in the art, connecting valves and lines, other than for one sequence, have not been illustrated on the drawing in order to avoid confusion. Thus, in the second phase of the operation, cooled methane chlorination reactor effluent from line 70 is fed to adsorber 61, the lean effluent from 61 passes through adsorber 63 which is simultaneously in the cooling phase, and adsorber 60 is beginning regeneration, with adsorber 62 completing its regeneration. In the next phase of the sequence, cooled methane chlorination reactor effluent from line 70 passes into adsorber 63 where the methyl chloride, etc., are adsorbed, lean effluent from adsorber 63 passes to adsorber 62, which is in the cooling phase, and adsorber 61 is beginning regeneration, with adsorber 60 completing regeneration. In the final phase, the cooled reactor effluent is fed to adsorber 62, the lean effluent passes to and cools adsorber 60, while adsorber 63 is beginning regeneration and adsorber 61 is completing regeneration.

More than four adsorption stages may be provided if desired, provided the heated methane feed is used to desorb the methyl chloride and methylene chloride in the given adsorber undergoing regeneration, and the lean reactor effluent from the particular adsorber undergoing the adsorption phase is used to cool the adsorber undergoing cooling. As employed throughout the specification and claims, the term "adsorption stage" includes one or more adsorbers, as for example, two adsorbers in series.

Any solid adsorbent material which has a high power of selectively adsorbing methyl chloride, methylene chloride, and the residual constituents of the chlorination reactor effluent may be used in the invention. For example, silica gels, activated carbon, activated alumina and various commercial molecular sieves may be employed. Activated carbon, which is particularly useful, is an amorphous form of carbon having a large surface area, on the order of from about 300 to about 2000 square meters per gram. The preferred type of this material is in the form of dense, hard granules or pellets. The term "molecular sieves" is used to designate the essentially dehydrated forms of crystalline, natural or synthetic, hydrosiliceous zeolites which contain various quantities of sodium, calcium, and aluminum, with or without metals. All, or a portion, of the sodium or calcium ions normally contained in the molecular sieve structure may be zeolitically replaced with a number of various ions. At the present time, there are several molecular sieves commercially available. Examples of sieves which may be used in the present process are those designated as 4A, 5A, 10X, 13X, and both synthetic and natural zeolites are adaptable to use in the method of the invention. For purposes of this invention, the particular adsorbent employed does not appear to be especially critical. However, activated carbon and zeolites of the 5A type are preferred.

In the case of the zeolite adsorbents, it is preferred the the sieves be "activated" in order for superior initial adsorption. "Activation" is accomplished merely by driving out any remaining water of hydration which is present interstitially, in order to open the cavities for the admission of the gas stream. The activation may be carried out as a separate step, or alternately, by merely heating the zeolites as part of the start up of the process.

The temperature of operation in the adsorption phase is significant and should be from about −50° C to about 20° C. A preferred temperature range is from about −30° C to about 10° C. Similarly, the temperature of the regeneration or stripping phase is significant and should be from about 100° C to about 400° C. and preferably from about 150° C. to about 250° C. In the cooling phase, the temperature should be from about −50° C to about 20° C. by virtue of the lean effluent from the chlorination reactor. The heat of adsorption of the methyl chloride, methylene chloride, and any residual chloroform or carbon tetrachloride is of minor significance in the regulation of the temperature in the adsorption phase. It will be appreciated by those skilled in the art that there is, for example, in the units of FIG. 1, a temperature gradient in the given adsorber undergoing stripping or regeneration since the stripping methane may be heated, illustratively, to approximately 200° C. or more before entering the adsorber, while the adsorber, when beginning regeneration, is approximately in the range from about −50° C to about 20° C. Heaters 9, 45, and 80 may be omitted if the feed methane is already heated or has a temperature, i.e., from about 100° C. to about 400° C., sufficient to give the desired temperature range in the stripping phase. Similarly, in the embodiments of FIGS. 2 and 3, there is a gradient, in the sequence shown, in the adsorbers 31 and 61, respectively, since both have just previously completed regeneration and are now being cooled.

The pressures employed, although at least slightly greater than atmospheric, are not particularly critical, and may depend to some extent upon pressures employed in other areas of the operation, such as for example, the pressure in the chlorination reactor. In some cases it may be desirable to operate the adsorption stage undergoing its adsorption phase at a higher pressure than the stage undergoing the desorption phase.

The amount of methyl chloride, methylene chloride, and any residual chloroform and carbon tetrachloride adsorbed in a given adsorption phase is not critical, and any desired amount may be adsorbed with due regard to limitations such as adsorber bed size, capacity of the adsorbent, and the economics of the situation. The time duration of each adsorption phase is related, inter alia, to factors such as the amount of material to be adsorbed, the size of the adsorbent bed, the degree of loading of the bed, the capacity of the adsorbent, and the pressure of the methane chlorination reactor effluent. In general, the adsorption phase will normally be continued in an adsorber until shortly before the adsorbent is fully loaded, and then transferred, to avoid loss or escape of the methyl chloride, etc. In the embodiment of FIG. 3, a phase duration of about one-half hour, based on the composition of the effluents, indicated, is suitable for slightly less than capacity (9,000 lbs) of an adsorber column having an activated carbon adsorbent bed with a bed diameter of about 11.2 feet and a bed height of about 10 feet.

As indicated previously, the invention is particularly applicable to the recovery of methyl chloride, methylene chloride, and any residual chloroform or carbon tetrachloride from cooled methane chlorination reactor effluents containing approximately 1% to about 35% of these materials, and which also contain large or significant amounts of relatively noncondensable gases. The invention is particularly applicable to the recovery of these materials from the cooled reactor effluents from oxychlorination reactor systems. In general, the reaction involves a catalyzed process in which gaseous chlorine or hydrogen chloride, or a mixture of hydrogen chloride and chlorine, is used as a chlorinating agent. The process further involves chlorination of methane with the chlorinating agent at a temperature of from about 300° C to about 600° C. and in the presence of an oxygen containing gas such as air, elemental oxygen, or air enriched with oxygen. As indicated, the process takes place in the presence of a catalyst, preferably a metal halide such as cupric chloride, which is generally impregnated on a carrier. It has been postulated that in these oxychlorination processes, the hydrogen chloride is oxidized to chlorine and water, and the chlorine reacts with the methane to form chlorinated methanes. Preferably, this reaction is carried out in a fluidized bed system. The effluent from the reactor which contains the chlorinated methanes, i.e., methyl chloride, methylene chloride, trichloromethane (chloroform), and carbon tetrachloride, is then passed through a condensation phase which will normally include a quench and further cooling phases, where, as indicated previously, the bulk of the chlorinated methanes is condensed. The quench, for example, may be chilled water having a temperature of from about 10° C. to about 15° C., and further cooling will reduce the temperature of the effluent to about −25° C. It is at this point that the recovery procedures involved in the present invention are significant since the "condensation" phase would have to be operated at great expense in order to achieve the separation of all of the lowboiling constituents (i.e., methyl chloride and methylene chloride) of the effluent stream. A recycle may also be provided at this point to increase the depth of chlorination of the chlorinated methanes or effect the desired equilibrium in the chlorination reactor.

In order to demonstrate more fully the practice of the invention, the following example is provided.

EXAMPLE

Methane, HCl, and air are combined in a reactor at a temperature of about 440° C. and a pressure of about 50 p.s.i.g. in the presence of a catalyst having a composition by weight percent of about 5.3 percent $CuCl_2$, 2.94 percent KCl, 8.73 percent $DiCl_3$, 2.3 percent $LaCl_3$, on an alpha-alumina support having a surface area of from about 10 to about 20 square meters per gram. HCl conversion is about 95 percent, with methane oxidation about 6.6 percent. The effluent from the reactor is then fed to a "condensation" stage wherein it is first quenched and then cooled in a series of stages to about −25° C. to remove the bulk of the chloroform and carbon tetrachloride.

The cooled effluent is then fed into a bank of adsorbers arranged in the manner of those described in FIG. 3. The temperature in adsorber 60 is approximately −20° C., and the pressure is approximately 40 p.s.i.g. On entering the adsorber 60, the effluent stream contains approximately 7% methyl chloride, 1% methylene chloride, and 0.1% of other chlorinated methanes. Adsorption of the chlorinated methanes is substantially complete. The lean effluent then passes through the adsorber 61 which is in its cooling phase, and reduces the temperature from approximately 200° C to −20° C. The warmed effluent is vented continously.

Simultaneously, feed methane is passed through heat exchanger 80, is raised to a temperature of approximately 200° C., and is used to strip the methyl chloride, etc., adsorbed in a previous step in adsorbed 63. The methane stream then is fed into adsorber 62 which is beginning regeneration and strips significant amounts of the chloromethanes from the unit. The exit temperature of the composite methane stream from adsorber 62 is initially approximately −20° C. The methane stream containing stripped chloromethanes is then fed through a cooling zone maintained at a temperature of −40° C. to recover the chloromethanes, and the methane is sent to the chlorination reactor.

Having thus described the invention, it is to be understood that other modifications, alterations and applications will become apparent to those skilled in the art without departing from the spirit thereof and that the scope thereof is limited only as defined in the claims appended hereto.

I claim:

1. A process for the recovery of methyl chloride and methylene chloride from a methane chlorination reactor effluent containing significant amounts of relatively noncondensable gases comprising cooling the reactor effluent to a temperature of from about −50° C. to about 20° C., passing the cooled reactor effluent to an adsorption stage containing a solid adsorbent material selected from the group consisting of silica gels, activated carbon, activated alumina, molecular sieves and combinations thereof to adsorb the methyl chloride and methylene chloride, stripping the methyl chloride and methylene chloride from the adsoprtion stage at a temperature of from about 100° C. to about 400° C. by the use of methane feed for the chlorination reactor, and subsequently cooling the adsorption stage.

2. A method for recovering methyl chloride and methylene chloride from a methane chlorination reactor effluent containing significant amounts of relatively noncondensable gases comprising (a) cooling the reactor effluent to a temperature of from about −50° C. to about 20° C.; (b) feeding the cooled methane chlorination reactor effluent to a first adsorption stage containing a solid adsorbent material selected from the group consisting of silica gels, activated carbon, activated alumina, molecular sieves and combinations thereof to adsorb methyl chloride and methylene chloride until a desired amount of the methyl chloride and methylene chloride is adsorbed and producing a lean reactor effluent; (c) stopping the flow of the cooled methane chlorination reactor effluent to the first adsorption stage and feeding the cooled reactor effluent to a second adsorption stage to adsorb methyl chloride and methylene chloride until a desired amount of the methyl chloride and methylene chloride is adsorbed and producing a lean reactor effluent, while simultaneously desorbing methyl chloride and methylene chloride adsorbed in the first adsorption stage at a temperature of from about 100° C to about 400° C. by the use of methane feed for the chlorination reactor, and recovering the methyl chloride and methylene chloride and methane feed, and then cooling the first adsorption stage with the lean reactor effluent from the second adsorption stage.

3. The process of claim 2 wherein the process is cyclic and wherein the lean effluent from each respective adsorption stage in its adsorption phase is used in cooling the respective adsorption stage which is in its cooling phase.

4. The process of claim 3 wherein the cooled chlorination reactor effluent contains minor amounts of chloroform and carbon tetrachloride, and wherein these materials are removed from the effluent.

5. A method for recovering methyl chloride and methylene chloride from a methane chlorination reactor effluent containing significant amounts of relatively noncondensable gases comprising
   a. cooling the reactor effluent to a temperature of from about −50° C to about 20° C.;
   b. feeding the cooled methane chlorination reactor effluent to a first adsorption stage containing a solid adsorbent material selected from the group consisting of silica gels, activated carbon, activated alumina, molecular sieves and combinations therof to adsorb methyl chloride and methylene chloride until a desired amount of the methyl chloride and methylene chloride is adsorbed, and producing a lean reactor effluent;
   c. stopping the flow of the cooled methane chlorination reactor effluent to the first adsorption stage and feeding said cooled reactor effluent to a second adsorption stage to adsorb methyl chloride and methylene chloride until a desired amount is adsorbed, producing a lean reactor effluent, while simultaneously desorbing the methyl chloride and methylene chloride adsorbed in the first adsorption stage at a temperature of from about 100° C to about 400° C. by the use of methane feed for the chlorination reactor, and recovering the methyl chloride and methylene chloride and the methane feed;
   d. stopping the flow of the cooled methane chlorination reactor effluent to the second adsorption stage and then feeding said cooled reactor effluent to a third adsorption stage to adsorb methyl chloride and methylene chloride until a desired amount is adsorbed, producing a lean reactor effluent, while simultaneously desorbing the methyl chloride and methylene chloride adsorbed in the second adsorption stage at a temperature of from about 100° C to about 400° C. by the use of methane feed for the chlorination reactor, and cooling the first adsorption stage with lean reactor effluent from the third adsorption stage, and recovering the methyl chloride and methylene chloride, and methane feed.

6. The process of claim 5 wherein the process is cyclic, and wherein the lean effluent from each respective adsorption stage in its adsorption phase is used in cooling the respective adsorption stage which is in its cooling phase.

7. The process of claim 6 wherein the cooled chlorination reactor effluent is from an oxychlorination reactor.

8. The process of claim 7 wherein the cooled chlorination reactor effluent contains minor amounts of chloroform and cabron tetrachloride, and wherein these materials are removed.

9. A process of recovering methyl chloride and methylene chloride from a methane chlorination reactor effluent containing significant amounts of relatively noncondensable gases comprising
   a. cooling the reactor effluent to a temperature of from about −50° C. to about 20° C.;
   b. feeding the cooled methane chlorination reactor effluent to a first adsorption stage containing a solid adsorbent material selected from the group consisting of silica gels, activated carbon, activated alumina, molecular sieves and combinations thereof to adsorb methyl chloride and methylene chloride until a desired amount is adsorbed, and producing a lean reactor effluent;
   c. stopping the flow of the cooled methane chlorination reactor effluent to the first adsorption stage and feeding said cooled reactor effluent to a second adsorption stage to adsorb methyl chloride and methylene chloride until a desired amount is adsorbed, producing a lean reactor effluent, while simultaneously beginning desorption of the methyl chloride and methylene chloride adsorbed in the first adsorption stage at a temperature of from about 100° C to about 400° C. by the use of methane feed for the chlorination reactor, and recovering the methyl chloride and methylene chloride, and methane feed;
   d. stopping the adsorbed of the cooled methane chlorination reactor effluent to the second adsorption stage and feeding said cooled reactor effluent to a third adsorption stage to adsorb methyl chloride and methylene chloride until a desired amount is adsorbed, and producing a lean reactor effluent, while simultaneously beginning desorption of the methyl chloride and methylene chloride adsorped in the second adsorption stage at a temperature of from about 100° C. by the use of heated methane feed for the chlorination reactor, and completing the desorption of the methyl chloride and methylene chloride adsorbed in the first adsorption stage, and recovering the methyl chloride and methylene chloride and methane feed;
   e. stopping the flow of the cooled methane chlorination reactor effluent to the third adsorption stage and feeding the cooled effluent to a fourth adsorption stage to adsorb methyl chloride and methylene chloride until a desired amount is adsorbed, and producing a lean reactor effluent; while simultaneously beginning desorption of the methyl chloride and methylene chloride adsorbed in the third adsorption stage at a temperature of from about 100° C to about 400° C. by the use of heated methane feed for the chlorination reactor, completing the desorption of the methyl chloride and methylene chloride adsorbed in the second adsorption stage, and cooling the first adsorption stage with the lean reactor effluent from the fourth adsorption stage.

10. The process of claim 9 wherein the process is cyclic, and wherein the lean effluent from each respective adsorption stage in its adsorption phase is used in cooling the respective adsorption stage which is in its cooling phase.

11. The process of claim 10 wherein the cooled chlorination reactor effluent is from an oxychlorination reactor.

12. The process of claim 7 wherein the cooled chlorination reactor effluent contains minor amounts of chloroform and carbon tetrachloride, and wherein these materials are removed.

* * * * *